(12) United States Patent
Kolomeyer et al.

(10) Patent No.: US 10,981,862 B2
(45) Date of Patent: *Apr. 20, 2021

(54) PHYSIOLOGICAL COOLING COMPOUNDS

(71) Applicant: Symrise, Inc., Teterboro, NJ (US)

(72) Inventors: Gennadiy Kolomeyer, Jacksonville, FL (US); David Sitko, Chicago, IL (US); Joe Snow, Kingsland, GA (US)

(73) Assignee: Symrise, Inc., Teterboro, NJ (US)

(*) Notice: Subject to any disclaimer, the term of this patent is extended or adjusted under 35 U.S.C. 154(b) by 112 days.

This patent is subject to a terminal disclaimer.

(21) Appl. No.: 15/578,726

(22) PCT Filed: Jun. 2, 2016

(86) PCT No.: PCT/US2016/035453
§ 371 (c)(1),
(2) Date: Dec. 1, 2017

(87) PCT Pub. No.: WO2016/196751
PCT Pub. Date: Dec. 8, 2016

(65) Prior Publication Data
US 2018/0179147 A1   Jun. 28, 2018

Related U.S. Application Data

(63) Continuation of application No. 14/730,853, filed on Jun. 4, 2015, now Pat. No. 10,173,966.

(51) Int. Cl.
| | | |
|---|---|---|
| *C07C 233/58* | (2006.01) | |
| *C07C 233/05* | (2006.01) | |
| *A61K 8/42* | (2006.01) | |
| *A23G 3/36* | (2006.01) | |
| *A23G 4/06* | (2006.01) | |
| *A23G 4/12* | (2006.01) | |
| *A61Q 11/00* | (2006.01) | |
| *A23L 27/20* | (2016.01) | |
| *C07C 231/02* | (2006.01) | |
| *C07C 51/60* | (2006.01) | |

(52) U.S. Cl.
CPC .............. *C07C 233/58* (2013.01); *A23G 3/36* (2013.01); *A23G 3/364* (2013.01); *A23G 4/06* (2013.01); *A23G 4/12* (2013.01); *A23L 27/20* (2016.08); *A23L 27/202* (2016.08); *A23L 27/204* (2016.08); *A61K 8/42* (2013.01); *A61Q 11/00* (2013.01); *C07C 51/60* (2013.01); *C07C 231/02* (2013.01); *C07C 233/05* (2013.01); *A23V 2002/00* (2013.01); *A61K 2800/244* (2013.01); *A61K 2800/40* (2013.01); *A61K 2800/592* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 4,150,052 A * | 4/1979 | Watson | A23G 3/36 |
| | | | 546/226 |
| 10,173,966 B2 * | 1/2019 | Kolomeyer | C07C 233/58 |

FOREIGN PATENT DOCUMENTS

GB    1457671 A * 12/1976    ............ A23L 1/226

* cited by examiner

*Primary Examiner* — Brian J Davis
(74) *Attorney, Agent, or Firm* — Michael P. Byrne; Wolter Van Dyke Davis, PLLC

(57) ABSTRACT

Physiological cooling compounds of the structure:

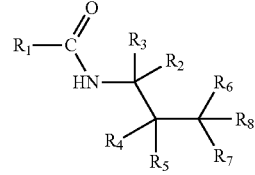

where $R_1$ is p-menthyl or 2,3,4-trimethylpent-3-yl group and $R_2$-$R_8$ are hydrogen or alkyl groups. The combination of $R_2$-$R_8$ is such that the N-alkyl group is a branched $C_5$ alkyl or branched or linear $C_6$-$C_8$ alkyl group. The new carboxamides are valuable sensory ingredients which provide long-lasting cooling sensation and freshness in personal care, oral care, cosmetic products, pharmaceutical preparations, confectionary, food and beverages.

9 Claims, 1 Drawing Sheet

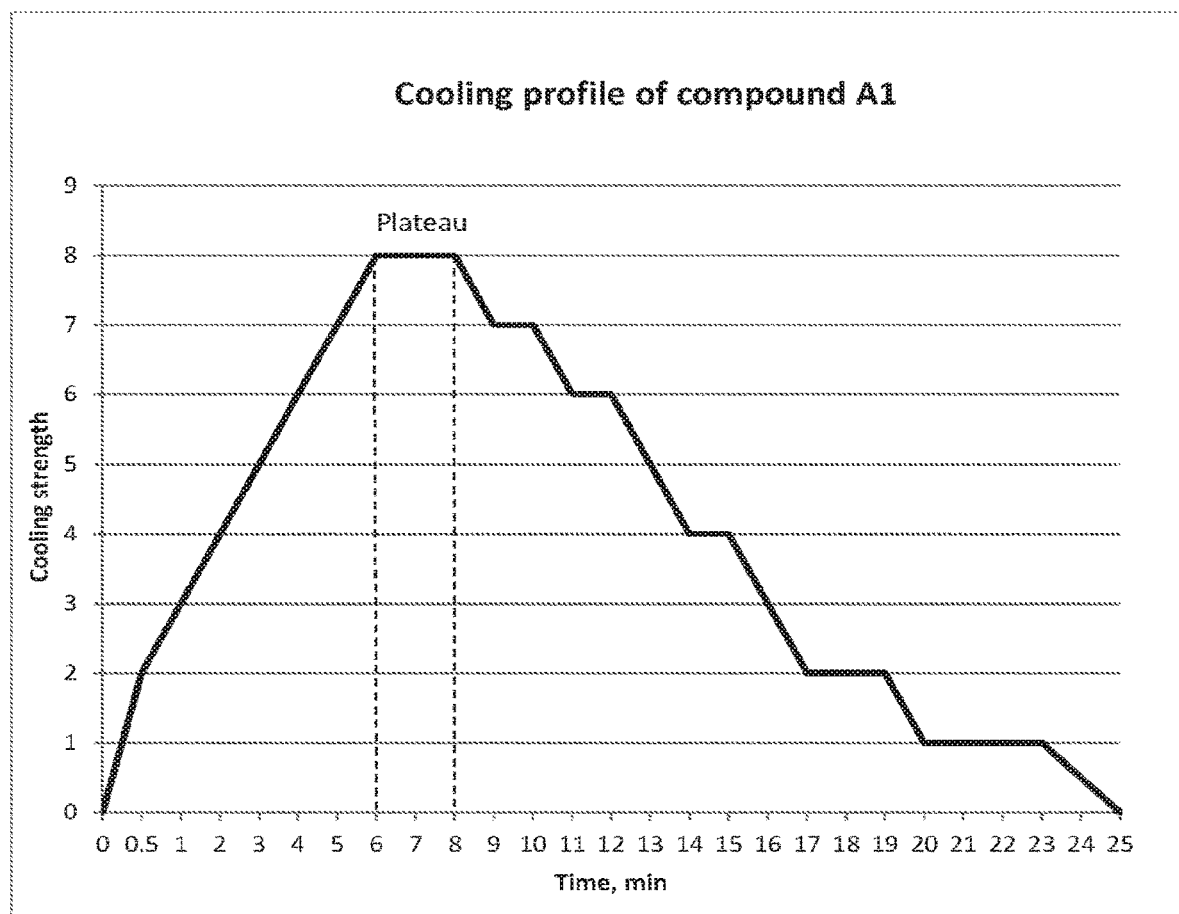

PHYSIOLOGICAL COOLING COMPOUNDS

CROSS-REFERENCE TO RELATED APPLICATIONS

This application is a National Stage entry of, and hereby claims priority to and the benefit of, PCT Application No. PCT/US16/35453, filed Jun. 2, 2016, which claims priority to and the benefit of U.S. Non-Provisional patent application Ser. No. 14/730,853, filed 4 Jun. 2015, and entitled "PHYSIOLOGICAL COOLING COMPOUNDS", the contents of which are herein incorporated by reference in their entirety.

FIELD

The disclosure relates generally to physiological cooling compositions and more specifically to organic physiological cooling compounds that impart a clean, fresh, and long-lasting cooling sensation in the mouth or on the skin when used as ingredients in confectionary, beverages, foodstuff, oral care, cosmetic and pharmaceutical preparations such as candies, chewing gums, alcoholic and non-alcoholic drinks, toothpastes and gels, mouthwashes, creams, lotions, aftershave preparations, pharmaceutical products, etc.

BACKGROUND

Physiological coolants provide cooling sensation upon contact with the body (skin, lips, mouth, nose, or throat) through chemical interaction as opposed to physical cooling caused by cold or evaporation. An array of chemical compounds may be classified as physiological coolants. Carboxamides, specifically para-menthane carboxamides, represent the most commercially successful group of physiological coolants. Carboxamides as physiological coolants were discovered in the 1970s. While many physiological cooling compounds have been synthesized and commercialized, there still is a need for new physiological cooling compounds that meet specific requirements in particular applications and impart the desired cooling sensation.

BRIEF DESCRIPTION OF THE DRAWINGS

These and other features, aspects, and advantages of the present disclosure will become better understood with reference to the following description and appended claims, and accompanying drawings where the FIGURE is a chart showing a cooling profile according to one embodiment disclosed herein.

DETAILED DESCRIPTION

The present disclosure may be understood more readily by reference to the following detailed description of preferred embodiments of the disclosure as well as to the examples included therein. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Disclosed are N-alkylamides of structure 1 that impart clean, fresh, and lasting cooling sensation.

Structure 1

The preferred $R_1$ in structure 1 is para-menthyl group (structure A) or 2,3,4-trimethylpent-3-yl group (structure B) and $R_2$-$R_8$ are hydrogen or alkyl groups.

Structure A

Structure B

The preferred combination of $R_2$-$R_8$ is such that the N-alkyl group is a branched $C_5$ alkyl or branched or linear $C_6$-$C_8$ alkyl group. In particular, $R_2$ is hydrogen, methyl or ethyl group; $R_3$-$R_5$ and $R_7$-$R_8$ are hydrogen or methyl group; and $R_6$ is hydrogen, methyl, n-propyl, n-butyl, isobutyl or n-pentyl group. The specific combinations of $R_2$-$R_8$ are given in table 1.

New carboxamides were prepared using the following reaction sequence, which involves converting a carboxylic acid to the corresponding chloroanhydride and reacting the latter with an appropriate amine:

Carboxylic acid → Chloro anhydride

Amine

Carboxamide

The carboxylic acids used as starting materials for the preparation of new carboxamides according to various embodiments are p-menthane-3-carboxylic acid, which leads to carboxamides of structure A ($R_1$ is para-menthyl; compounds A1-A15), and 2,3-dimethyl-2-(propan-2-yl)butanoic acid, which leads to carboxamides of structure B ($R_1$ is 2,3,4-trimethylpent-3-yl; compounds B1-B15). The preferred isomer of p-menthane carboxylic acid is (1R,2S,5R)-2-isopropyl-5-methylcyclohexanecarboxylic acid.

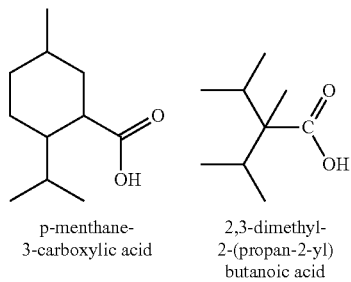

p-menthane-3-carboxylic acid    2,3-dimethyl-2-(propan-2-yl)butanoic acid

The amines used for the preparation of new carboxamides are monoalkylamines, where alkyl is a branched $C_5$ alkyl group or branched or linear $C_6$-$C_8$ alkyl group. The specific combinations of $R_2$-$R_8$ are provided in table 1. The examples of amines include tertiary-amylamine, isoamylamine, neopentylamine, 1,2-dimethylpropylamine, 2-aminopentane, 2-methylbutylamine, 3-aminopentane, hexylamine, 4-methyl-2-aminopentane, heptylamine, 2-aminoheptane, octylamine, 2-ethylhexylamine, 2-amino-6-methylheptane, and t-octylamine.

Various embodiments relate to compounds of the general formula:

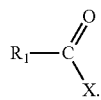

$R_1$ may be selected from p-menthyl and 2,3,4-trimethylpent-3-yl group. X may be an alkylamine moiety, having an alkyl group selected from a branched $C_5$ alkyl, a linear $C_6$-$C_8$ alkyl group, and a branched $C_6$-$C_8$ alkyl group. According to various embodiments X may be a moiety according to the formula:

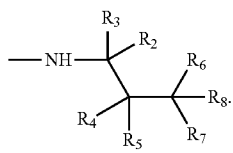

$R_2$-$R_8$ may be selected from the group consisting of hydrogen, and $C_1$-$C_5$ alkyl groups. $R_2$ may be selected from a hydrogen, a methyl group, and an ethyl group. $R_3$-$R_5$ may be selected from a hydrogen, and a methyl group. $R_7$-$R_8$ may be selected from a hydrogen, and a methyl group. $R_6$ may be selected from a hydrogen, a methyl group, an n-propyl group, an n-butyl group, an isobutyl group, and an n-pentyl group.

The compounds according to various embodiments may be included in a wide variety of compositions, including but not limited to personal care compositions, oral care compositions, cosmetic products, pharmaceutical preparations, confectionaries, foods, beverages, and combinations thereof. The compound may be present a composition in an amount within a range having a lower limit and/or an upper limit. The range can include or exclude the lower limit and/or the upper limit. The lower limit and/or upper limit can be selected from about 0.01, 0.05, 0.1, 0.5, 1, 5, 10, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000, 10500, 11000, 11500, 12000, 12500, 13000, 13500, 14000, 14500, and 15000 ppm. For example, according to certain preferred embodiments, the compound may be present a composition in an amount of from 0.01 to 10,000 ppm.

The compositions according to various embodiments may include any other desirable components. For example, the compositions may include a second physiological coolant. The second physiological coolant may be selected from WS-3, WS-23, WS-5, WS-12, menthyl lactate, menthylhydroxybutyrate, and combinations thereof.

The compositions according to various embodiments may include the compounds according to various embodiments in an amount within a range having a lower limit and/or an upper limit. The range can include or exclude the lower limit and/or the upper limit. The lower limit and/or upper limit can be selected from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99% by weight based on the total weight of the composition. For example, according to certain preferred embodiments, the compositions according to various embodiments may include the compounds according to various embodiments in an amount of from 5-95% by weight based on the total weight of the composition.

The compositions may be a liquid eutectic mixture at a temperature within a range having a lower limit and/or an upper limit. The range can include or exclude the lower limit and/or the upper limit. The lower limit and/or upper limit can be selected from about 0, 5, 10, 15, 20, 25, 30, 35, 40, 45, 50, 55, 60, 65, 70, 75, 80, 85, 90, 95, and 100 degrees Celsius. For example, according to certain preferred embodiments, the compositions may be a liquid eutectic mixture at a temperature greater than 0 degrees Celsius.

The compositions may further include a solvent. The solvent may be selected from propylene glycol, ethanol, benzyl alcohol, ethyl acetate, 1-carvone, 1-menthone, triacetin, short-chain triglycerides, medium-chain triglycerides, and combinations thereof. As used herein, the term "short-chain triglycerides" refer to triglycerides having tails of fewer than six carbon atoms in length. As used herein, the term "medium-chain triglycerides" refer to triglycerides having tails of from six to 12 carbon atoms in length.

The compositions may be encapsulated with an encapsulation agent selected from Cyclodextrins, maltodextrins, gum arabic, hydrogenated vegetable fats, hydrogenated vegetable oils, synthetic polymers, synthetic resins, and combinations thereof.

Various embodiments relate to a method that includes converting at least one carboxylic acid to at least one chloroanhydride; and reacting the at least one chloroanhydride with at least one amine to produce at least one compound of the formula:

$R_1$ may be selected from p-menthyl and 2,3,4-trimethylpent-3-yl group. X may be a moiety according to the formula:

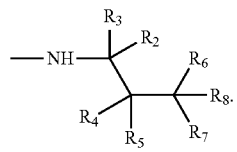

X may be an alkylamine moiety with an alkyl group selected from a branched $C_5$ alkyl, a linear $C_6$-$C_8$ alkyl group, and a branched $C_6$-$C_8$ alkyl group. According to various embodiments, the at least one carboxylic acid may be selected from p-menthane-3-carboxylic acid, and 2,3-dimethyl-2-(propan-2-yl)butanoic acid, and combinations thereof. According to various embodiments, the at least one amine may be selected from tertiary-amylamine, isoamylamine, neopentylamine, 1,2-dimethylpropylamine, 2-aminopentane, 2-methylbutylamine, 3-aminopentane, hexylamine, 4-methyl-2-aminopentane, heptylamine, 2-aminoheptane, octylamine, 2-ethylhexylamine, 2-amino-6-methylheptane, and t-octylamine, and combinations thereof. $R_2$-$R_8$ may be selected from hydrogen, and $C_1$-$C_5$ alkyl groups. $R_2$ may be selected from a hydrogen, a methyl group, and an ethyl group. $R_3$-$R_5$ may be selected from a hydrogen, and a methyl group. $R_7$-$R_8$ may be selected from a hydrogen, and a methyl group. $R_6$ may be selected from a hydrogen, a methyl group, an n-propyl group, an n-butyl group, an isobutyl group, and an n-pentyl group.

According to various embodiments, the step of converting the at least one carboxylic acid to the at least one chloroanhydride may be performed in the presence of one selected from thionyl chloride, phosphorus trichloride, and combinations thereof.

Various embodiments relate to a product produced by a process according to various embodiments described herein. For example, various embodiments relate to a product produced by a process that includes converting at least one carboxylic acid selected from the group consisting of p-menthane-3-carboxylic acid, and 2,3-dimethyl-2-(propan-2-yl)butanoic acid, and combinations thereof to at least one chloroanhydride in the presence of one selected from the group consisting of thionyl chloride, phosphorus trichloride, and combinations thereof; and reacting the at least one chloroanhydride with at least one selected from the group consisting of tertiary-amylamine, isoamylamine, neopentylamine, 1,2-dimethylpropylamine, 2-aminopentane, 2-methylbutylamine, 3-aminopentane, hexylamine, 4-methyl-2-aminopentane, heptylamine, 2-aminoheptane, octylamine, 2-ethylhexylamine, 2-amino-6-methylheptane, and t-octylamine, and combinations thereof.

The product, so produced, may have the formula:

$R_1$ may be selected from p-menthyl and 2,3,4-trimethylpent-3-yl group. X may be alkylamine moiety, having an alkyl group selected from a branched $C_5$ alkyl, a linear $C_6$-$C_8$ alkyl group, and a branched $C_6$-$C_8$ alkyl group. X may be a moiety according to the formula:

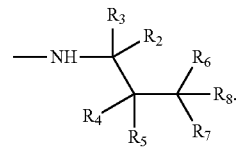

$R_2$-$R_8$ may be selected from hydrogen, and $C_1$-$C_5$ alkyl groups.

EXAMPLES

Examples of new physiological coolants prepared from the carboxylic acids and amines described above are provided in Table 1.

TABLE 1

| Compound | $R_2$ | $R_3$ | $R_4$ | $R_5$ | $R_6$ | $R_7$ | $R_8$ | m.p. °C. |
|---|---|---|---|---|---|---|---|---|
| A1 | Me | Me | H | H | H | H | H | 133.1 |
| A2 | H | H | H | H | Me | Me | H | 69.6 |
| A3 | H | H | Me | Me | H | H | H | 152.4 |
| A4 | Me | H | Me | H | H | H | H | 160.2 |
| A5 | Me | H | H | H | Me | H | H | 154.5 |
| A6 | H | H | Me | H | Me | H | H | 92.8 |
| A7 | Et | H | H | H | H | H | H | 192.6 |
| A8 | H | H | H | H | n-Pr | H | H | 58.8 |
| A9 | Me | H | H | H | Me | Me | H | 152.6 |
| A10 | H | H | H | H | n-Bu | H | H | liquid |
| A11 | Me | H | H | H | n-Pr | H | H | liquid |
| A12 | H | H | H | H | n-Pe | H | H | liquid |
| A13 | H | H | Et | H | n-Pr | H | H | liquid |
| A14 | Me | H | H | H | i-Bu | H | H | 146.7 |
| A15 | Me | Me | H | H | Me | Me | Me | 107 |
| B1 | Me | Me | H | H | H | H | H | liquid |
| B2 | H | H | H | H | Me | Me | H | 72.2 |
| B3 | H | H | Me | Me | H | H | H | 65.9 |
| B4 | Me | H | Me | H | H | H | H | 88.4 |
| B5 | Me | H | H | H | Me | H | H | 98.0 |
| B6 | H | H | Me | H | Me | H | H | 67.1 |
| B7 | Et | H | H | H | H | H | H | 105.0 |
| B8 | H | H | H | H | n-Pr | H | H | liquid |
| B9 | Me | H | H | H | Me | Me | H | 83.7 |
| B10 | H | H | H | H | n-Bu | H | H | liquid |
| B11 | Me | H | H | H | n-Pr | H | H | 46.9 |
| B12 | H | H | H | H | n-Pe | H | H | liquid |
| B13 | H | H | Et | H | n-Pr | H | H | 82.5 |
| B14 | Me | H | H | H | i-Bu | H | H | 59.4 |
| B15 | Me | Me | H | H | Me | Me | Me | liquid |

The new carboxamides A1-A15 and B1-B15 were evaluated for their cooling ability by a sensory panel. The evaluation included tasting the 20 ppm aqueous solutions of new carboxamides and rating their maximum cooling strength on a 1-10 scale. In addition, the time at which maximum cooling strength was reached, how long the maximum strength was observed (so called cooling plateau), and the longevity of cooling sensation were recorded. The FIGURE represents a typical cooling profile, using compound A1 as an example. The obtained results (table 2), were compared with two most commonly used commercial cooling compounds WS-3 and WS-23 which belong to the same class of N-alkyl carboxamides. While various methods exist for evaluation of cooling compounds, we have chosen the parameters that allow to assess the practical aspects of new compounds that reflect their potential value as commercial sensory ingredients.

TABLE 2

| Compound | Peak cooling strength | Time to reach peak cooling, min | Time period at peak cooling, min | Longevity of cooling sensation, min |
|---|---|---|---|---|
| A1 | 8 | 6 | 2 | 25 |
| A2 | 7 | 5 | 2 | 23 |
| A3 | 7 | 4 | 3 | 22 |
| A4 | 5 | 3 | 2 | 20 |
| A5 | 7 | 4 | 2 | 21 |
| A6 | 6 | 3 | 2 | 20 |
| A7 | 6 | 3 | 2 | 16 |
| A8 | 6 | 5 | 2 | 29 |
| A9 | 3 | 5 | 4 | 15 |
| A10 | 5 | 4 | 1 | 19 |
| A11 | 2 | 8 | 2 | 15 |
| A12 | 2 | 6 | 4 | 10 |
| A13 | —[a] | — | — | — |
| A14 | —[a] | — | — | — |
| A15 | 2 | 4 | 6 | 14 |
| B1 | —[a] | — | — | — |
| B2 | 2 | 3 | 2 | 12 |
| B3 | 3 | 3 | 3 | 15 |
| B4 | 4 | 3 | 2 | 14 |
| B5 | 6 | 2 | 3 | 15 |
| B6 | 4 | 3 | 2 | 17 |
| B7 | 4 | 4 | 2 | 14 |
| B8 | 3 | 4 | 1 | 17 |
| B9 | 5 | 4 | 2 | 18 |
| B10 | —[a] | — | — | — |
| B11 | —[a] | — | — | — |
| B12 | —[a] | — | — | — |
| B13 | —[a] | — | — | — |
| B14 | —[a] | — | — | — |
| B15 | —[a] | — | — | — |
| WS-3 | 5 | 2 | 2 | 11 |
| WS-23 | 4 | 2 | 2 | 7 |

[a] Not cooling under tested conditions

Surprisingly, many new compounds surpassed the known N-alkyl carboxamides in peak cooling strength, the time to reach the peak, and longevity. The differences in cooling properties of the corresponding compounds in series A and B as well as within the same series highlight the unexpected nature of these results. Thus, the same amine was utilized to prepare compounds A1 and B1. Compound A1 is one of the most potent coolants found among the N-alkyl p-menthane carboxamides, while compound B1 does not possess any cooling properties. There is no discernible pattern that would allow to predict variations in cooling properties within the two series of N-alkyl carboxamides based on structures of either the carboxylic acid or amine.

Table 3 shows the threshold values of N-alkyl-p-menthanecarboxamides according to the following formula:

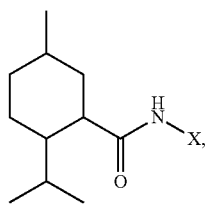

where the moiety X is specified as indicated in Table 3, which has been obtained from U.S. Pat. No. 4,150,052, titled N-substituted paramenthane carboximides.

TABLE 3

| X | Alkyl type | Threshold, µg |
|---|---|---|
| Methyl | $C_1$ | 1.1 |
| Ethyl | $C_2$ | 0.3 |
| Propyl | $C_3$ primary, linear | 0.8 |
| Isopropyl | $C_3$ secondary, linear | 0.5 |
| Butyl | $C_4$ primary, linear | 1.4 |
| Isobutyl | $C_4$ primary, branched | 0.9 |
| sec-Butyl | $C_4$ secondary, linear | 0.7 |
| tert-Butyl | $C_4$ tertiary, branched | 0.4 |
| Amyl | $C_5$ primary, linear | 3 |
| Decyl | $C_{10}$ primary, linear | 10 |

As used herein, the term "threshold" means the amount of a particular compound needed to produce a cooling sensation. Threshold is inversely correlated with cooling intensity: the lower the threshold, the higher the cooling strength.

Trends observed in this teaching: 1) the threshold bottoms at $C_2$ for the strongest coolant within this set of compounds. The compound, known as WS-3, became the most successful commercial coolant; 2) cooling ability progressively decreases from $C_2$ through $C_5$ and even more to $C_{10}$; 3) within the same size of alkyl group, the secondary and tertiary are more potent than the primary; and 4) branched are more potent than linear.

Based on these observations, the compound A8, having a primary linear $C_6$ alkyl, should be expected to possess a lower cooling strength than WS-3 ($C_2$) or A4 (secondary, branched $C_5$). However, its peak cooling strength exceeds both WS-3 and A4. Similarly, the predicted strength of the compound A9 (secondary, branched $C_6$), should have been higher than A8 (primary, linear $C_6$) but in reality, A8 is significantly stronger. The compound A15, having a tertiary branched alkyl group, should have been one of the strongest coolants and certainly much stronger than the isomeric A12 with a primary, linear alkyl group. However it's only as strong as A12 and much weaker than other coolants.

Based on sensory evaluation of their cooling properties, the compounds according to various embodiments can be used as flavor ingredients that impart the desirable fresh and long lasting cooling sensation. The preferred compounds are A1, A2, A3, A4, A5, A6, A7, A8, A10, B4, B5, and B9.

Examples 2-7 demonstrate and confirm the usefulness of new cooling compounds as flavor ingredients for the consumer goods products such as chewing gum, mouthwash, pressed mints, hard-boiled candy, toothpaste, and other oral care, cosmetic and confectionary formulations, and pharmaceutical preparations.

These examples reveal the high potency of the new physiological coolants according to various embodiments, in particular their long lasting effect in various applications. Glycine, N-[[5-methyl-2-(1-methylethyl)cyclohexyl]carbonyl]-, ethyl ester (WS-5) was chosen for comparative examples because of its wide use and high cooling potency among the conventional commercially available physiological coolants.

Example 1

Example 1 illustrates a general procedure for the preparation of compounds A1-A15. A 50% solution of 0.1 moles of 2-isopropyl-5-methylcyclohexanecarbonyl chloride in heptane (prepared from 0.1 moles of (1R,2S,5R)-2-isopropyl-5-methylcyclohexanecarboxylic acid and thionyl chloride or phosphorus trichloride using conventional procedures) was added to a 50% solution of 0.3 moles of an appropriate amine in heptane at 20 degrees Celsius over 1 hour while agitating. Then the reaction mixture was slowly heated to 60 degrees Celsius and was held at this temperature for 1 hour. An equal volume of water was added at 60 degrees Celsius, the reaction mixture was agitated for 30 minutes, settled for 1 hour, and the layers were separated. The organic layer was washed with an equal volume of 3% aqueous hydrochloric acid and water. The heptane solution of the obtained p-menthanecarboxamide was dried by removing water as an azeotrop with heptane by refluxing at atmospheric pressure with a Dean-Stark trap. If needed, some heptane was removed to allow the p-menthanecarboxamide to crystallize upon cooling to 0 degrees Celsius. After filtration and drying, the purity of the obtained p-menthanecarboxamides was determined by GC analysis. The obtained carboxamides were recrystallized from heptane or ethyl acetate to achieve a higher than 99% purity. The molar yields of the isolated p-menthanecarboxamides were in the 80-90% range. Some of the obtained p-menthanecarboxamides are liquids. These compounds were purified by fractional microdistillation at 0.5-1 mm Hg residual pressure. Starting amines and structures of the obtained p-menthanecarboxamides are given in Table 4.

TABLE 4

| Compound | Starting amine | Structure | Peak Strength | Alkyl type |
|---|---|---|---|---|
| A1 | tertiary-amylamine | 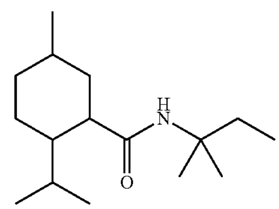 [SMILES: CCC(C)(C)NC(=O)C1CC(C)CCC1C(C)C] | 8 | $C_5$ tertiary, branched |
| A2 | isoamylamine | 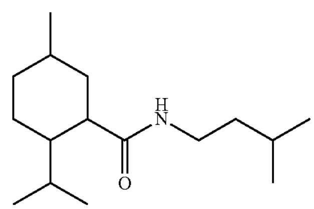 [SMILES: CC(C)CCNC(=O)C1CC(C)CCC1C(C)C] | 7 | $C_5$ primary, branched |
| A3 | neopentylamine | 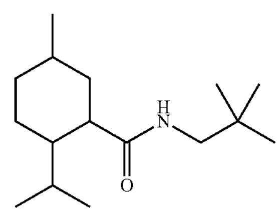 [SMILES: CC1CCC(C(C)C)C(C(=O)NCC(C)(C)C)C1] | 7 | $C_5$ primary, branched |
| A4 | 1,2-dimethylpropylamine | 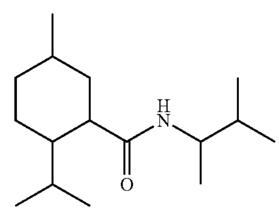 [SMILES: CC1CCC(C(C)C)C(C(=O)NC(C)C(C)C)C1] | 5 | $C_5$ secondary, branched |
| A5 | 2-aminopentane | 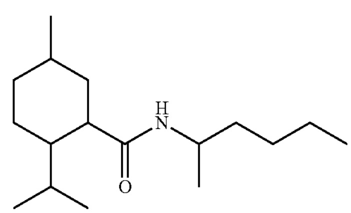 [SMILES: CCCCC(C)NC(=O)C1CC(C)CCC1C(C)C] | 7 | $C_5$ secondary, linear |
| A6 | 2-methylbutylamine | 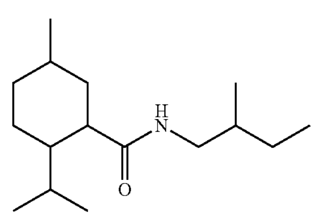 [SMILES: CCC(C)CNC(=O)C1CC(C)CCC1C(C)C] | 6 | $C_5$ primary, branched |

TABLE 4-continued
| Compound | Starting amine | Structure | Peak Strength | Alkyl type |
|---|---|---|---|---|
| A7 | 3-aminopentane | 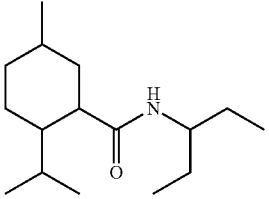 [SMILES: CCC(CC)NC(=O)C1CC(C)CCC1C(C)C] | 6 | $C_5$ secondary, linear |
| A8 | hexylamine | 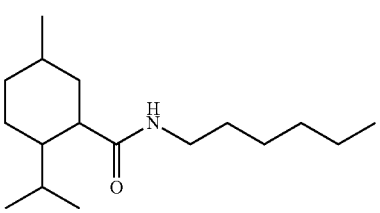 [SMILES: CCCCCCNC(=O)C1CC(C)CCC1C(C)C] | 6 | $C_6$ primary, linear |
| A9 | 4-methyl-2-aminopentane | 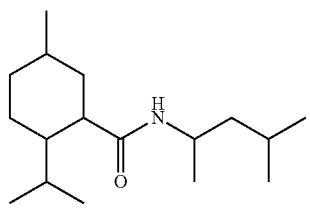 [SMILES: CC(C)CC(C)NC(=O)C1CC(C)CCC1C(C)C] | 3 | $C_6$ secondary, branched |
| A10 | heptylamine | 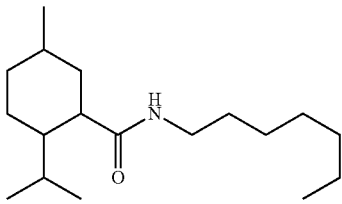 [SMILES: CCCCCCCNC(=O)C1CC(C)CCC1C(C)C] | 5 | $C_7$ primary, linear |
| A11 | 2-aminoheptane | 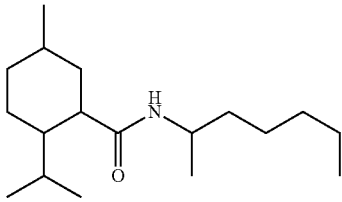 [SMILES: CCCCCC(C)NC(=O)C1CC(C)CCC1C(C)C] | 2 | $C_7$ secondary, linear |
| A12 | octylamine | 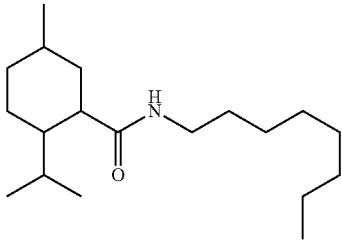 [SMILES: CCCCCCCCNC(=O)C1CC(C)CCC1C(C)C] | 2 | $C_8$ primary, linear |
| A13 | 2-ethylhexylamine | 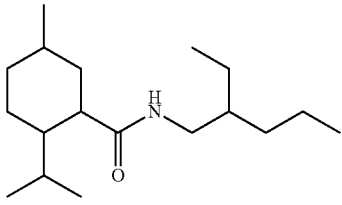 [SMILES: CCCC(CC)CNC(=O)C1CC(C)CCC1C(C)C] | —[a] | $C_8$ secondary, branched |

TABLE 4-continued

| Compound | Starting amine | Structure | Peak Strength | Alkyl type |
|---|---|---|---|---|
| A14 | 2-amino-6-methylheptane | 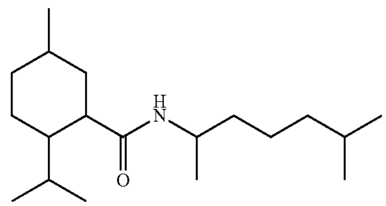 [SMILES: CC(C)CCCC(C)NC(=O)C1CC(C)CCC1C(C)C] | —[a] | $C_8$ secondary, branched |
| A15 | tertiary-octylamine | 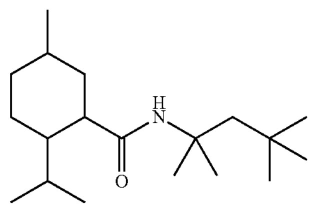 [SMILES: CC1CCC(C(C)C)C(C(=O)NC(C)(C)CC(C)(C)C)C1] | 2 | $C_8$ tertiary, branched |

Example 2

Example 2 illustrates the general procedure for the preparation of compounds B1-B15. A 50% solution of 0.1 moles of 2-isopropyl-2,3-dimethylbutanoyl chloride in heptane (prepared from 0.1 moles of 2,3-dimethyl-2-(propan-2-yl) butanoic acid and thionyl chloride or phosphorus trichloride using conventional procedures) was added to a 50% solution of 0.3 moles of an appropriate amine in heptane at 20 degrees Celsius over 1 hour while agitating. Then the reaction mixture was slowly heated to 60 degrees Celsius and was held at this temperature for 1 hour. An equal volume of water was added at 60 degrees Celsius, the reaction mixture was agitated for 30 minutes, settled for 1 hour, and the layers were separated. The organic layer was consecutively washed with an equal volume of 3% aqueous hydrochloric acid and water. The heptane solution of the obtained 2,3-dimethyl-N-alkyl-2-isopropylbutanamide was dried by removing water as an azeotrop with heptane by refluxing at atmospheric pressure with a Dean-Stark trap. If needed, some heptane was removed to allow the p-menthanecarboxamide to crystallize upon cooling to 0 degrees Celsius. After filtration and drying, the purity of the obtained carboxamides was determined by GC analysis. The obtained carboxamides were recrystallized from heptane or ethyl acetate to achieve a higher than 99% purity. Molar yields of the isolated 2,3-dimethyl-N-alkyl-2-isopropylbutanamides were in the 80-90% range. Some of the obtained carboxamides are liquids. These compounds were purified by fractional microdistillation at 0.5-1 mm Hg residual pressure. Starting amines and structures of the obtained 2,3-dimethyl-N-alkyl-2-isopropylbutanamides are given in Table 5.

TABLE 5

| Compound | Starting amine | Structure |
|---|---|---|
| B1 | tertiary-amylamine | |
| B2 | isoamylamine | 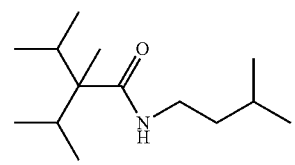 [SMILES: CC(C)CCNC(=O)C(C)(C(C)C)C(C)C] |
| B3 | neopentylamine | 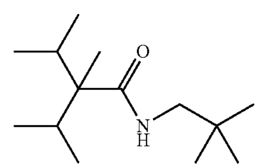 [SMILES: CC(C)C(C)(C(=O)NCC(C)(C)C)C(C)C] |
| B4 | 1,2-dimethyl-propylamine | 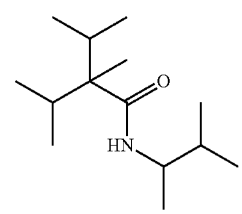 [SMILES: CC(C)C(C)NC(=O)C(C)(C(C)C)C(C)C] |
| B5 | 2-aminopentane | 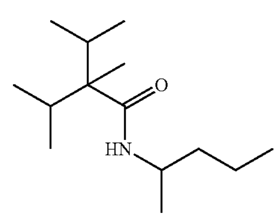 [SMILES: CCCC(C)NC(=O)C(C)(C(C)C)C(C)C] |
| B6 | 2-methyl-butylamine | 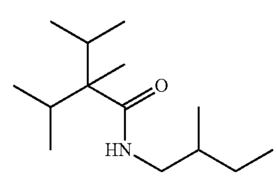 [SMILES: CCC(C)CNC(=O)C(C)(C(C)C)C(C)C] |

TABLE 5-continued

| Compound | Starting amine | Structure |
|---|---|---|
| B7 | 3-aminopentane | 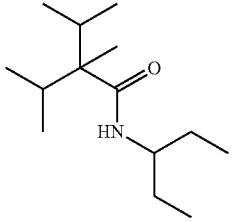 [SMILES: CCC(CC)NC(=O)C(C)(C(C)C)C(C)C] |
| B8 | hexylamine | 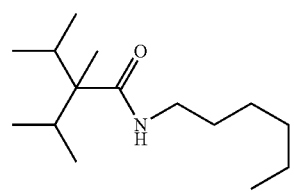 [SMILES: CCCCCCNC(=O)C(C)(C(C)C)C(C)C] |
| B9 | 4-methyl-2-aminopentane | 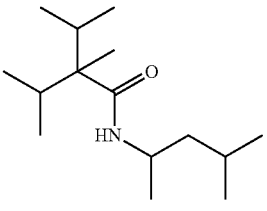 |
| B10 | heptylamine | 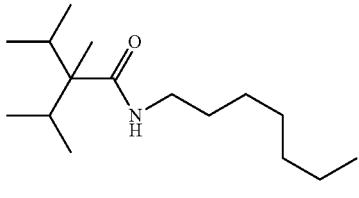 [SMILES: CCCCCCCNC(=O)C(C)(C(C)C)C(C)C] |
| B11 | 2-aminoheptane | 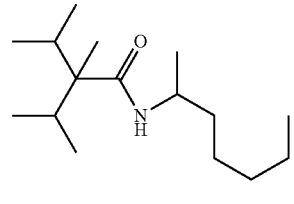 [SMILES: CCCCCC(C)NC(=O)C(C)(C(C)C)C(C)C] |
| B12 | octylamine | 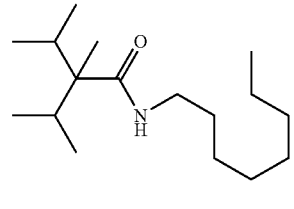 [SMILES: CCCCCCCCNC(=O)C(C)(C(C)C)C(C)C] |
| B13 | 2-ethylhexylamine | 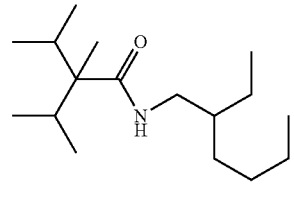 [SMILES: CCCCC(CC)CNC(=O)C(C)(C(C)C)C(C)C] |
| B14 | 2-amino-6-methylheptane | 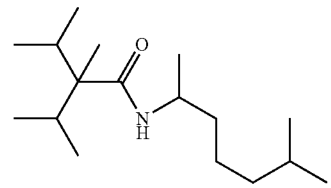 [SMILES: CC(C)CCCC(C)NC(=O)C(C)(C(C)C)C(C)C] |
| B15 | tertiary-octylamine | 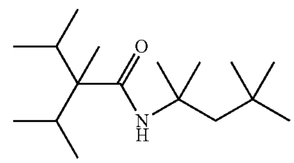 [SMILES: CC(C)C(C)(C(=O)NC(C)(C)CC(C)(C)C)C(C)C] |

Example 3

Various new coolants, as disclosed herein were tested in chewing gum at 1,000 ppm concentration and their impact was evaluated against the control (a known coolant WS-5). The compositions of chewing gums and evaluation results of the cooling strength and longevity of the new coolants during and after a 30 min chewing are given in Table 6.

TABLE 6

|  | Sample 3-1 (control) | Sample 3-2 | Sample 3-3 | Sample 3-4 |
|---|---|---|---|---|
| Sorbitol | 55.85 | 55.85 | 55.85 | 55.85 |
| Gum base | 30.0 | 30.0 | 30.0 | 30.0 |
| Glycerin | 8.0 | 8.0 | 8.0 | 8.0 |
| Water | 3.9 | 3.9 | 3.9 | 3.9 |
| Aspartame | 0.025 | 0.025 | 0.025 | 0.025 |
| Acesulfame potassium | 0.025 | 0.025 | 0.025 | 0.025 |
| Mint flavor | 2.0 | 2.0 | 2.0 | 2.0 |
| Compound A1 | — | 0.1 | — | — |
| Compound A2 | — | — | 0.1 | — |
| Compound A8 | — | — | — | 0.1 |
| WS-5 | 0.1 | — | — | — |
| Cooling strength | Strong | Strong | Strong | Strong |
| Cooling peak, min | 5-10 | 8-12 | 9-12 | 10-15 |
| Cooling longevity, min | 40 | 48 | 55 | 60 |

These examples demonstrate the long-lasting cooling effect of the new coolants according to various embodiments in chewing gums. They also provide a lasting fresh aftertaste.

Example 4

Select physiological coolants according to various embodiments were tested in an alcohol-free mouthwash and their impact was evaluated against the control (a known coolant WS-5). The composition of mouthwash and evaluation results of the cooling strength and longevity are given in Table 7.

TABLE 7

|  | Sample 4-1 (control) | Sample 4-2 | Sample 4-3 | Sample 4-4 |
|---|---|---|---|---|
| Water | 90.427 | 90.427 | 90.427 | 90.427 |
| Glycerin | 7.02 | 7.02 | 7.02 | 7.02 |
| Sorbitol | 1.4 | 1.4 | 1.4 | 1.4 |
| Poloxamer 407 | 0.75 | 0.75 | 0.75 | 0.75 |
| Sucralose | 0.04 | 0.04 | 0.04 | 0.04 |
| Sodium benzoate | 0.08 | 0.08 | 0.08 | 0.08 |
| Mint flavor | 0.28 | 0.28 | 0.28 | 0.28 |
| Compound A1 | — | 0.03 | — | — |
| Compound A2 | — | — | 0.003 | — |
| Compound A8 | — | — | — | 0.003 |
| WS-5 | 0.003 | — | — | — |
| Cooling strength | Strong | Strong | Strong | Strong |
| Cooling peak, min | 4-6 | 5-10 | 8-12 | 5-12 |
| Cooling longevity, min | 23 | 28 | 31 | 35 |

These examples demonstrate that compounds A1, A2, and A8 provide a superior long-lasting cooling effect comparing with a congenital cooling compound WS-5.

Example 5

New cooling compound according to compound A2 was tested in toothpaste and its impact was evaluated against two controls (no coolant and a known coolant WS-5) and in combination with WS-5. The compositions of toothpastes and evaluation results of the cooling strength and longevity are given in Table 8.

TABLE 8

|  | Sample 5-1 (control 1) | Sample 5-2 (control 2) | Sample 5-3 | Sample 5-4 |
|---|---|---|---|---|
| Toothpaste base | 99.5 | 99.475 | 99.475 | 99.475 |
| Mint flavor | 0.5 | 0.5 | 0.5 | 0.5 |
| Compound A2 | — | — | 0.025 | 0.0125 |
| WS-5 | — | 0.025 | — | 0.0125 |
| Cooling strength | Weak | Strong | Strong | Strong |
| Cooling peak, min | 2 | 5 | 7 | 7 |
| Cooling longevity, min | 15 | 20 | 35 | 35 |

These examples demonstrate a superior and longer lasting effect of the new compound A2 and a benefit of using it in applications in combination with a known physiological coolant.

Example 6

Select physiological coolants according to various embodiments were tested in pressed mints and their impact was evaluated against the control (no physiological coolant) and a known coolant WS-5. The compositions of pressed mints and evaluation results of the cooling strength and longevity are given in Table 9.

TABLE 9

|  | Sample 6-1 (control 1) | Sample 6-2 (control 2) | Sample 6-3 | Sample 6-4 | Sample 6-5 |
|---|---|---|---|---|---|
| Sorbitol | 98.54 | 98.52 | 98.52 | 98.52 | 98.52 |
| Sucralose | 0.06 | 0.06 | 0.06 | 0.06 | 0.06 |
| Magnesium stearate | 1.0 | 1.0 | 1.0 | 1.0 | 1.0 |
| Mint flavor | 0.4 | 0.4 | 0.4 | 0.4 | 0.4 |

TABLE 9-continued

|  | Sample 6-1 (control 1) | Sample 6-2 (control 2) | Sample 6-3 | Sample 6-4 | Sample 6-5 |
|---|---|---|---|---|---|
| Compound A1 | — | — | 0.02 | — | — |
| Compound A2 | — | — | — | 0.02 | — |
| Compound A8 | — | — | — | — | 0.02 |
| WS-5 | — | 0.02 | — | — | — |
| Cooling strength | Weak | Strong | Strong | Strong | Strong |
| Cooling peak, min | 2-3 | 2-3 | 4-5 | 4-5 | 7-8 |
| Cooling longevity, min | 5 | 15 | | 25 | 35 |

Evaluation of pressed mint samples containing new physiological coolants according to various embodiments demonstrated their superiority in cooling strength and longevity against menthol (control 1, mint flavor with menthol) and a conventional coolant WS-5 (control 2).

Example 7

Compound A2 was tested in hard boiled candy and evaluated against controls. The compositions of had boiled candy and evaluation results are presented in Table 10.

TABLE 10

|  | Sample 7-1 (control 1) | Sample 7-2 (control 2) | Sample 7-3 |
|---|---|---|---|
| Cooked base | 99.57 | 99.55 | 99.55 |
| Peppermint flavor | 0.4 | 0.4 | 0.4 |
| Blue 1 (5% solution) | 0.03 | 0.03 | 0.03 |
| WS-5 | — | 0.02 | — |
| Compound A2 | — | — | 0.02 |
| Cooling strength | Weak | Strong | Strong |
| Cooling peak, min | 2-3 | 4-6 | 7-8 |
| Cooling longevity, min | 10 | 12 | 30 |

The results demonstrated the long-lasting cooling impact of compound A2 in hard candy and its superiority against both control samples.

Although the various embodiments have been described in considerable detail with reference to certain preferred versions thereof, other versions are possible. Therefore, the spirit and scope of the appended claims should not be limited to the description of the preferred versions contained herein. All the features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A method comprising:
    converting at least one carboxylic acid to at least one chloroanhydride; and
    reacting the at least one chloroanhydride with at least one amine to produce at least one compound of the formula:

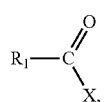

wherein $R_1$ is selected from the group consisting of p-menthyl and 2,3,4-trimethylpent-3-yl group, and wherein X is an alkylamine moiety having an alkyl group selected from the group consisting of a branched $C_5$ alkyl, a linear $C_6$-$C_8$ alkyl group, and a branched $C_6$-$C_8$ alkyl group, and wherein converting the at least one carboxylic acid to the at least one chloroanhydride is performed in the presence of one selected from the group consisting of thionyl chloride, phosphorus trichloride, and combinations thereof.

2. The method according to claim 1, wherein the at least one carboxylic acid is selected from the group consisting of p-menthane-3-carboxylic acid, and 2,3-dimethyl-2-(propan-2-yl)butanoic acid, and combinations thereof.

3. The method according to claim 2, wherein the at least one amine is selected from the group consisting of tertiary-amylamine, isoamylamine, neopentylamine, 1,2-dimethylpropylamine, 2-aminopentane, 2-methylbutylamine, 3-aminopentane, hexylamine, 4-methyl-2-aminopentane, heptylamine, 2-aminoheptane, octylamine, 2-ethylhexylamine, 2-amino-6-methylheptane, and t-octylamine, and combinations thereof.

4. The method according to claim 1, wherein the alkylamine moiety has a formula:

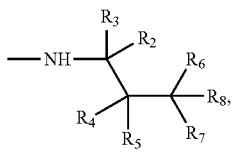

wherein $R_2$-$R_8$ of the alkyl group of the alkylamine moiety are selected from the group consisting of hydrogen, and $C_1$-$C_5$ alkyl groups, provided that, as a whole, the alkyl group of the alkylamine moiety remains selected from the group consisting of the branched $C_5$ alkyl, the linear $C_6$-$C_8$ alkyl group, and the branched $C_6$-$C_8$ alkyl group.

5. The method according to claim 4, wherein $R_2$ is selected from the group consisting of a hydrogen, a methyl group, and an ethyl group.

6. The method according to claim 4, wherein $R_3$-$R_5$ are selected from the group consisting of a hydrogen, and a methyl group.

7. The method according to claim 4, wherein R7-R8 are selected from the group consisting of a hydrogen, and a methyl group.

8. The method according to claim 4, wherein $R_6$ is selected from the group consisting of a hydrogen, a methyl group, an n-propyl group, an n-butyl group, an isobutyl group, and an n-pentyl group.

9. A product produced by a process comprising:

converting at least one carboxylic acid selected from the group consisting of p-menthane-3-carboxylic acid, and 2,3-dimethyl-2-(propan-2-yl)butanoic acid, and combinations thereof to at least one chloroanhydride; and reacting the at least one chloroanhydride with at least one selected from the group consisting of tertiary-amylamine, isoamylamine, neopentylamine, 1,2-dimethylpropylamine, 2-aminopentane, 2-methylbutylamine, 3-aminopentane, hexylamine, 4-methyl-2-aminopentane, heptylamine, 2-aminoheptane, octylamine, 2-ethylhexylamine, 2-amino-6-methylheptane, and t-octylamine, and combinations thereof, and wherein converting the at least one carboxylic acid to the at least one chloroanhydride is performed in the presence of one selected from the group consisting of thionyl chloride, phosphorus trichloride, and combinations thereof.

* * * * *